United States Patent [19]

Cipollina et al.

[11] Patent Number: 4,490,616
[45] Date of Patent: Dec. 25, 1984

[54] CEPHALOMETRIC SHIELD

[76] Inventors: John J. Cipollina, 190-18 Haywood Rd., Hollis, N.Y. 11423; Laurance E. Jerrold, 82 Laurel Dr., Massapequa Park, N.Y. 11762

[21] Appl. No.: 429,021

[22] Filed: Sep. 30, 1982

[51] Int. Cl.³ .......................... G21C 11/00; G21F 1/00
[52] U.S. Cl. .................................. 250/515.1; 378/145
[58] Field of Search .......................... 250/515.1, 516.1; 378/145, 38

[56] References Cited

U.S. PATENT DOCUMENTS

| | | | |
|---|---|---|---|
| 1,191,274 | 7/1916 | Brayton | 250/516.1 |
| 2,962,589 | 11/1960 | Dlouhy et al. | 250/515.1 |
| 3,304,423 | 2/1967 | Medwedeff | . |
| 3,539,805 | 11/1970 | Shiller et al. | 378/38 |
| 4,223,229 | 9/1980 | Persico et al. | 250/515.1 |
| 4,286,170 | 8/1981 | Moti | 250/516.1 |

Primary Examiner—Bruce C. Anderson
Attorney, Agent, or Firm—Mitchell B. Wasson; Martin P. Hoffman; Charles W. Fallow

[57] ABSTRACT

A shield used to prevent an excessive amount of radiation to be absorbed by a patient during a cephalometry procedure. The shield consists of a lead sheet which is supported by a cephalometric head holder. A hole is provided in the shield for cooperation with the cephalometric head holder to insure proper positioning of the shield. Additionally, a brad, staple, screw or the like is used to insure that the head holder remains immobile during the cephalometry procedure.

10 Claims, 3 Drawing Figures

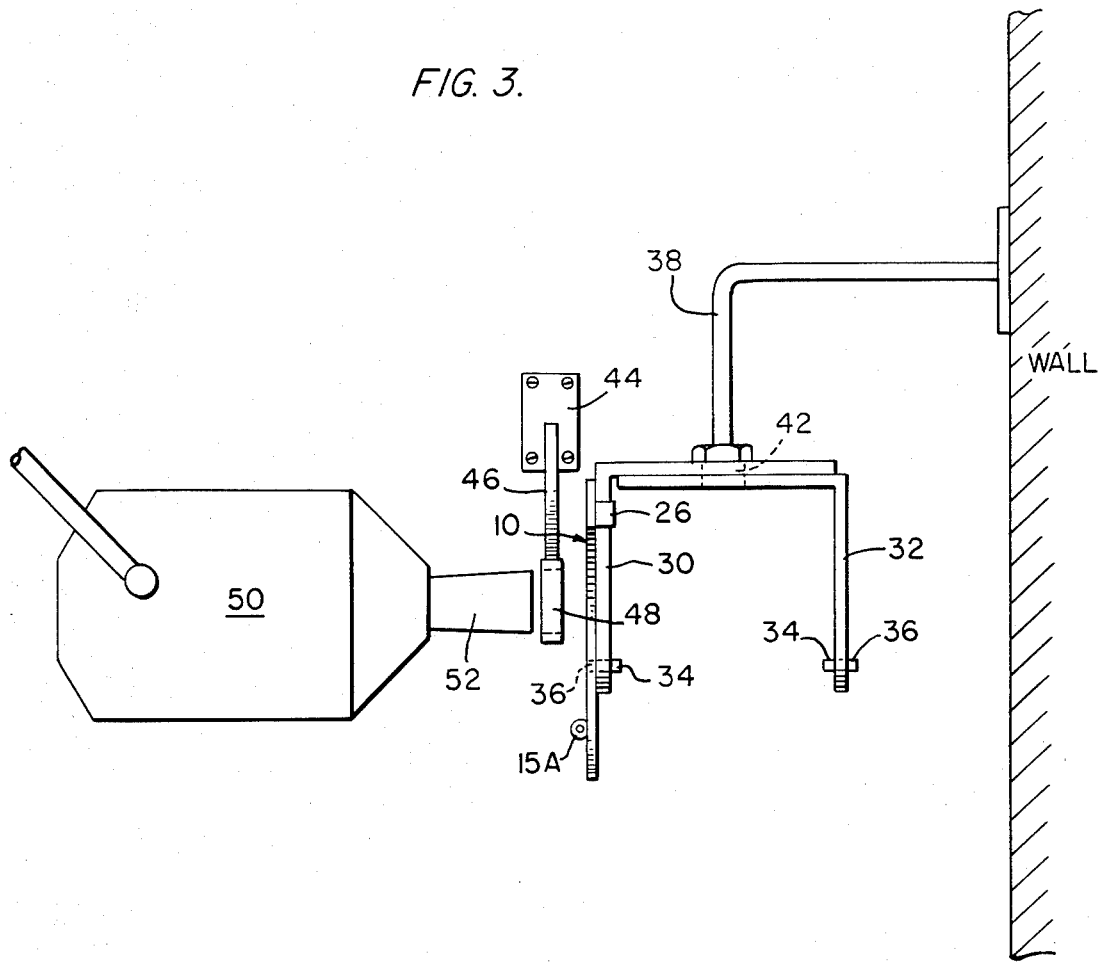

CEPHALOMETRIC SHIELD

BACKGROUND OF THE INVENTION

Various diagnostic and therapeutic procedures have been developed utilizing X-ray or other types of radiation. These procedures include utilizing X-rays for determining the presence of various conditions as well as techniques for treating malignancies.

However, the unnecessary and uncontrolled subjection of the human body, or portions thereof, to radiation can have many deleterious effects. The medical and dental professions have accordingly taken steps attempting to reduce, as far as possible, the subjection of patients to this harmful radiation, occurring either inadvertently or during intended treatment to various parts of the body, or resulting from stray, scattered and surplus rays.

It has been found that even very limited amounts of exposure to radiation, especially in children, occasionally causes damage to such glands as the pituitary and thyroid. In efforts to avoid such problems, techniques and apparatuses have been developed which attempt to absorb or shield various body areas of the patient from undesired exposure or from stray or scattered X-rays such as those which normally tend to scatter from the principal stream of X-rays. Preferably, the only X-rays allowed to contact human tissue are those necessary for the specific procedure. U.S. Pat. Nos. 2,962,589, issued to Dlouhy; 3,304,523, issued to Medwedeff; 4,223,229, issued to Persico et al; and 4,286,170, issued to Moti are examples of different devices used to protect a patient during a radiation procedure.

The patent to Dlouhy describes a diagnostic chair which includes a radiation shield directly attached to the chair. The shield contains a block which is slid into position against the patient's neck. A thumb screw is loosened in order for the shield to be pivoted and lie flat against the neck area.

The patent to Persico et al illustrates an oral radiation protector for protecting teeth, gingiva, peridontal bones, salivary glands, and adjacent body areas against the effects of radiation therapy. The protector consists of an intraoral shield which is placed in the patient's mouth. The shield portion is generally curvilinear in shape and is attached to encompass the lower front portion of the head. However, neither of these references describes a device which protects the head during a cephalometric diagnostic procedure.

SUMMARY OF THE INVENTION

The present invention is directed to a shield which is used to protect various portions of a patient's head, neck, and skull which need not be subjected to radiation during a cephalometric diagnostic procedure utilizing X-ray or similar radiation.

The shield consists of a relatively planar piece of material which is impervious to X-rays. This planar portion can be utilized in conjunction with a cephalometric head holder to insure that the cephalometric shield is properly positioned with respect to the X-ray machine. Additionally, a screw, brad, staple or the like is used in conjunction with the cephalometric head holder to insure that the shield is properly held immobile.

Furthermore, since radiation is reduced to a smaller portion of the patient's face and skull, the size of the film which is utilized in the cephalometric procedure can be reduced.

Additionally, an alternate embodiment utilizes a removable shield in conjunction with the shield and cephalometric head holder to vary the portion of the face which is subjected to X-rays.

The above and other features of the present invention will be more fully understood when considered in connection with the following description of a typical device embodying the invention as shown in the accompanying drawings.

BRIEF DESCRIPTION OF THE DRAWINGS

FIG. 3 is a side elevation showing the entire cephalometric unit.

DETAILED DESCRIPTION OF THE DRAWINGS

Figure 1:
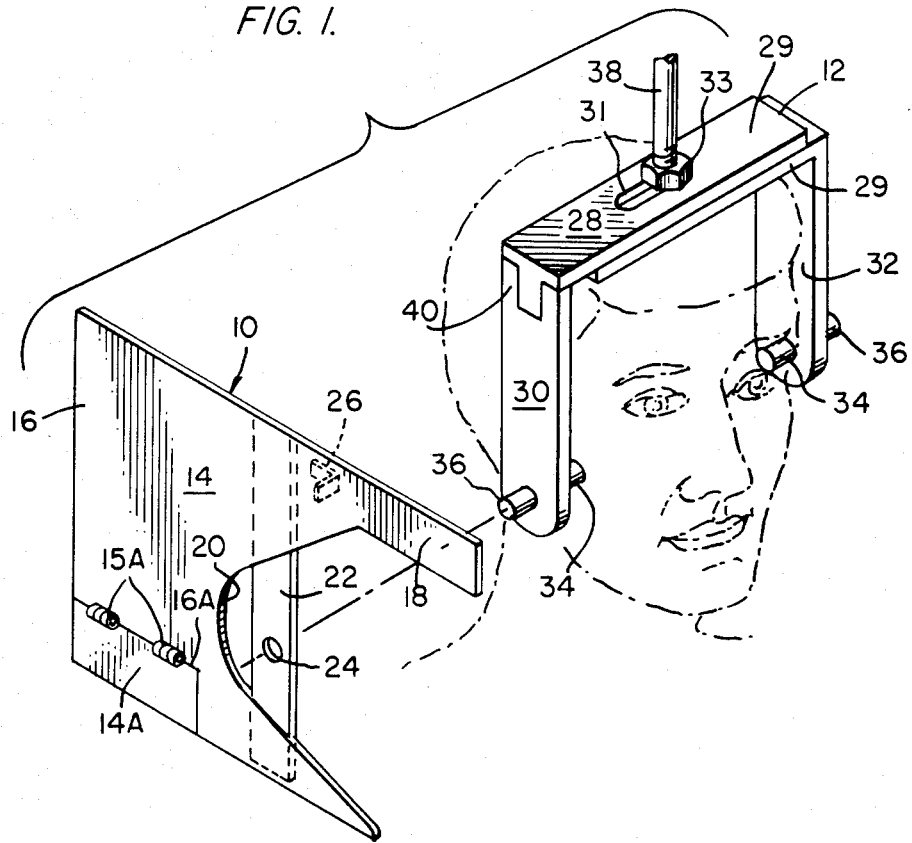
FIG. 1 is a perspective view showing the cephalometric head holder and the shield.

FIG. 1 shows a perspective view of the cephalometric shield 10 used in conjunction with a cephalometric head holder 12. It should be noted that the head holder is a functional portion of a standard cephalometric X-ray unit and is not considered to be claimed as a portion of the present invention, except to the extent to which the cephalometric shield is attached thereto during an X-ray procedure. The shield 10 consists of a planar portion 14 which is configured to cover the portion of a patient's skull and face which is not to be subjected to X-ray or similar radiation emanating from a standard radiation source such as an X-ray machine. It should be pointed out that the portion 14 does not have to be planar but could be constructed as curvilinear to better protect the patient's skull. Although the exact dimensions of the planar portion 14 are not particularly important, it should be noted that a portion measuring approximately 15" by 10" has been utilized with success. The 15" portion is measured from a distal end 16 to a portion 18 which can be utilized as a holder for a soft tissue screen. A curvilinear portion 20 is cut from the planar portion 14 to allow radiation to be directed to that portion of the skull which undergoes the cephalometric procedure. Although the exact material which is utilized for the planar portion 14 is unimportant, it is crucial that the material be impervious to penetrating radiation. Lead or similar material can be used for this purpose. A flap portion 14A of the planar portion 14 is configured to rotate along an axis formed by line 16A to expose the base of the skull should that be desired. A pair of hinges 15A are utilized to facilitate the elevation of this flap portion. a rectangular or trapezoidal member 22 pervious to X-rays, is provided between two points on the surface of the cut out portion 20. This rectangular or trapezoidal portion contains an aperture 24 which is used in conjunction with the cephalometric head holder to positively position the cephalometric shield and the head of the patient. If the cephalometric head holder does not have an extra lateral ear rod 36, one can easily be attached to 30 in the same plane as ear rods 34 of the head holder.

The cephalometric head holder is attached to a wall by a cylindrical or otherwise shaped rod 38 and consists of two planar rectangular members 28 and 29 which are adapted to fit over the top of the patient's skull. Either member 28 and 29 is provided with a slot 31 such that the total length of those members can be adjusted to fit all skull sizes. A nut 33 is provided on the rod 38 and is used to tighten the fit of the members 28 and 29. Two vertical ear rod support members 30 and 32 are attached orthoganally with respect to members 28 and 29. These support members 30 and 32 are adapted to run along the sides of the patient's face and skull. A swivel connection 40 is provided for ease of placement of the head holder over the patient's skull. Two relatively short rods 34 extend from the inner surface of each of the members 30 and 32. These rods are to be inserted slightly into the patient's ears, thereby positively maintaining the patient's head in a specific arrangement with respect to the X-ray equipment. Rods 36 are provided on the outside of members 30 and 32 in axial alignment with rods 34. These rods 36 are either provided on the head holder by the manufacturer or can easily be attached thereto and are used to engage with an aperture 24 of the shield 10 to positively maintain the holder in the proper position to insure that only a minimum amount of radiation is directed into the patient's skull and facial areas.

A staple 26 is provided on the inside or top surface of the cephalometric shield and engages the vertical ear rod support 30 to insure that the cephalometric shield does not rotate counterclockwise due to the ectopical weight distribution of the lead shield. Additionally, a brad, or screw which is mounted in the same position on the surface of the shield can be utilized to effect the same stability.

Figure 2:
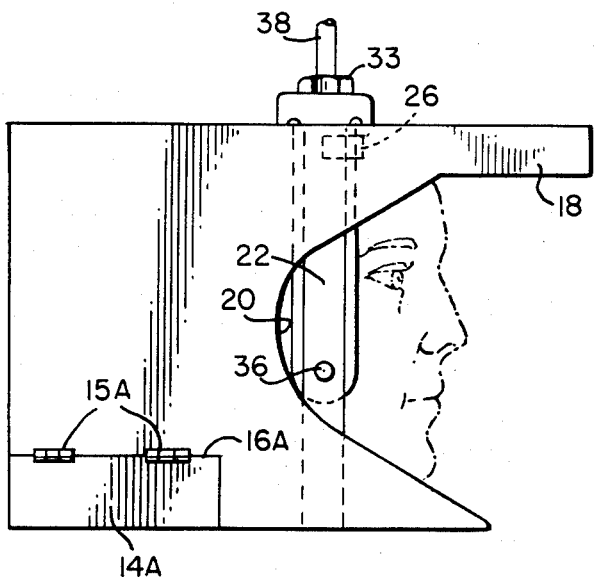
FIG. 2 is a side view showing the cephalometric head holder with the shield in place.

FIG. 2 illustrates the cephalometric head holder with the cephalometric shield properly in place.

FIG. 3 shows a side elevation of the entire system with the cephalometric shield 10 attached to the cephalometric head holder. The X-ray machine 50 contains a tube 52 which is properly aligned with respect to the cephalometric shield 10 by a fixator 46 consisting of an aperture 48 attached to a wall by a plate 44.

Although the cephalometric shield is used in conjunction with the head holder which is standard equipment with most cephalometric X-ray machines, the use of the shield is not to be construed as being so limited. For example, a strap can be attached to two sides of the shield which can then encircle the patient's head or neck to maintain the shield in its proper orientation.

While the invention has been described and illustrated in its several preferred embodiments, it should be understood that the invention is not to be limited to the precise details herein illustrated and described since the same may be carried out in other ways falling within the scope of the invention as claimed.

What is claimed is:

1. A radiation shield adapted to be used in combination with an X-ray tube and a cephalometric X-ray head holder containing alignment ear rods comprising:
   a shield surface constructed of a material which is impervious to radiation, said surface adapted to be placed between the skull of the patient and the X-ray beam; and
   alignment means attached to said shield surface, said alignment means containing an aperture for cooperation with the alignment ear rods of the cephalometric head holder.

2. A radiation shield as claimed in claim 1 further including a means of stabilizing said shield against movement.

3. A radiation shield as claimed in claim 1 wherein said shield surface is planar.

4. A radiation shield as claimed in claim 1 wherein said shield surface contains a flap which can be elevated to expose the base of the skull.

5. A radiation shield as claimed in claims 2 or 3 wherein said shield surface contains a flap which can be elevated to expose the base of the skull.

6. A radiation shield adapted to be used in combination with a cephalometric X-ray head holder and X-ray tube comprising:
   a shield surface constructed of a material which is impervious to radiation, said surface adapted to be placed between the skull of the patient and the X-ray beam;
   alignment rods attached to the cephalometric head holder, and
   alignment means attached to said shield surface, said alignment means containing an aperture for cooperation with said alignment ear rods of the cephalometric head holder.

7. A radiation shield as claimed in claim 6 further including a means of stabilizing said shield against movement.

8. A radiation shield as claimed in claim 6 wherein said shield surface is planar.

9. A radiation shield as claimed in claim 6 wherein said shield surface contains a flap which can be elevated to expose the base of the skull.

10. A radiation shield as claimed in claims 7 or 8 wherein said shield surface contains a flap which can be elevated to expose the base of the skull.

* * * * *